United States Patent [19]

Rich et al.

[11] Patent Number: 5,058,785
[45] Date of Patent: Oct. 22, 1991

[54] APPARATUS AND METHODS FOR DONNING AND REMOVING GLOVES

[75] Inventors: Clayton E. Rich; Jesse D. Dye, both of Shelley, Id.; Robert Bremers, Louisville, Colo.

[73] Assignee: Successs Builders International, Idaho Falls, Id.

[21] Appl. No.: 546,301

[22] Filed: Jun. 29, 1990

[51] Int. Cl.⁵ ...................... A47G 25/80; A47G 25/90
[52] U.S. Cl. .................................................... 223/111
[58] Field of Search ............. 223/111; 2/DIG. 7, 168, 2/160

[56] References Cited

U.S. PATENT DOCUMENTS

| | | | |
|---|---|---|---|
| 1,938,685 | 12/1933 | Breulis et al. | 223/111 |
| 1,996,377 | 4/1935 | Hinchen | 223/111 |
| 2,741,410 | 4/1956 | La Violette | 223/111 |
| 3,067,001 | 12/1962 | McCollum | 223/111 X |
| 3,237,821 | 3/1966 | Hayne et al. | 223/111 |
| 3,695,493 | 10/1972 | Karr | 223/111 |
| 4,002,276 | 1/1977 | Poncy et al. | 223/111 |
| 4,069,913 | 1/1978 | Harrigan | 206/278 |
| 4,155,494 | 5/1979 | Poncy et al. | 223/111 |
| 4,228,935 | 10/1980 | Madray | 223/111 |
| 4,275,812 | 6/1981 | Poncy et al. | 206/278 |
| 4,889,266 | 12/1989 | Wight | 223/111 |
| 4,898,309 | 2/1990 | Fischer | 223/111 |
| 4,915,272 | 4/1990 | Vlock | 223/111 |

Primary Examiner—Werner H. Schroeder
Assistant Examiner—Bibhu Mohanty
Attorney, Agent, or Firm—Workman, Nydegger and Jensen

[57] ABSTRACT

An apparatus for facilitating the application and removal of gloves. The apparatus comprises a vacuum system wherein a vacuum pump evacuates air from a vacuum chamber, such that a glove positioned over an opening into the vacuum chamber is inflated. The glove is positioned over the opening by a stiffening ring attached to the wrist portion of the glove which has a diameter larger than the diameter of the opening. The apparatus includes a device for controlling the vacuum pump operation speed such that the amount of vacuum pressure used and the amount of glove inflation obtained may be adjusted to both higher and lower settings. Thus, the apparatus is particularly adapted for use in various geographical locations and elevations. The device is also ambidextrous in its use such that right and left hands can be gloved by the same device. One handed application is facilitated by an electrical foot switch operating the vacuum pump.

16 Claims, 3 Drawing Sheets

APPARATUS AND METHODS FOR DONNING AND REMOVING GLOVES

BACKGROUND

1. The Field of the Invention

This invention relates to apparatus for facilitating the donning and removal of elastomeric gloves. More particularly, the apparatus relates to the use of vacuum pressure which inflates the gloves to facilitate the donning and removal of the gloves. Importantly, the apparatus allows the user to control the level of vacuum pressure needed to inflate the gloves.

2. Background of the Invention

Gloves are becoming increasingly indispensable in many areas of today's working world. There is a growing awareness of the necessity of gloves for sanitary reasons, for prevention of the spread of AIDS and other diseases, and for general cleanliness and protection.

In the medical field, personnel such as surgeons, nurses, paramedics, and dentists, working in emergency rooms, intensive care units, dental offices, and many other similar health care environments, are all regularly required to use elastic examination gloves to stop the spread of infectious organisms, from the infected patient to the attendant or from the attendant to other patients. The busy schedules of these professionals and the crucial nature of their work require that their time not be unnecessarily wasted in donning and removing the gloves.

In addition to the medical field, other fields such as food handling and preparation and chemical and biotechnical research are rapidly realizing the need for protection against product and/or worker contamination.

In many restaurants, fast-food operations, and other places where food is handled, the use of gloves is essential to preventing contamination of food. In these places, contamination can be disastrous because of the large number of people served each day. Unfortunately, it is difficult and time-consuming to don the necessary elastic gloves. Since "fast" food service is what is promised by most places today, there is usually no extra time to waste struggling with donning and removing gloves.

Another problem today is the expense of having to use new gloves each time gloves are needed. In some applications the same glove may be safely reused. However, it is difficult to remove the glove without inverting it or without touching its exterior surface. Efforts to do so often result in tearing of the glove or otherwise rendering the glove unusable.

Although various attempts to solve these problems have been made by those skilled in the art, to date there has not been devised an apparatus that has fully succeeded in solving the foregoing glove-donning and removing problems.

One approach to solve these problems has been to use a vacuum system in which vacuum pressure causes the glove to inflate, allowing the user to insert his or her hand into the glove without difficulty. However, the amount of vacuum pressure necessary to properly inflate the glove varies depending on the altitude at which the device is being used. Unfortunately, the existing devices using a vacuum system do not have means for controlling the amount of vacuum pressure applied. Thus, the devices can only function properly in areas which match the size and power output of the vacuum pump. For example, a device made to be used effectively within the Rocky Mountain states would not function effectively near sea level. Problems such as underinflation, overinflation, or inflation of only the palm area of the glove often arise.

An additional problem with these devices now in the art is the small hand area in which the vacuum is created. Most of the devices provide a cylindrical vacuum area in which larger hands cannot be outstretched comfortably. Therefore, a single prior art device cannot be used for both women with small hands and men with much larger hands. In addition, a device which adequately inflates gloves for a small woman's hand would not adequately inflate gloves for a large man's hand.

Another problem with many devices now in the art is the difficulty of maintaining and cleaning the devices. A device with removable parts, which can be assembled and disassembled with ease, would greatly facilitate cleaning and would be beneficial to the users to whom efficiency as well as cleanliness is crucial.

Yet another problem with many existing devices is the need for two hands or an assistant to apply or remove the gloves. This is particularly a problem for handicapped or injured people who do not have the use of both hands. These people cannot don or remove gloves by themselves. They are forced to wait for assistance. A worker who has one hand occupied is in the same position. In order to don the glove, he must either set down whatever he is holding, or again wait for assistance. Many times, both options are either inconvenient or even impossible.

One example of this is in the medical profession, where someone might find it impossible to set down the object he or she is holding because of risk of infection or risk of damage to the object. He or she might find that waiting for assistance is also impossible. At times, having to wait could mean the difference between minor and major injury or possibly even the difference between life and death.

Another example is in the fast food industry. A worker may not wish to stop performing with one hand whatever task he or she is performing, or, if a worker is holding food in one hand, it may be unsanitary to set it down while donning a new glove. Furthermore, the need to wait for assistance defeats the object of "fast" food.

Additionally, there are instances where only one glove is needed. In several existing devices, both hands must be gloved at the same time. These devices do not have the option for donning a glove onto only one hand.

In view of the foregoing, it would be an advance in the art to provide an apparatus for quick, easy, and convenient donning and removing of elastomeric gloves for which only one hand is needed for its use. It would be a further advance in the art to provide an apparatus for removing gloves which does not tear or invert the gloves such that the gloves can be easily reused.

An additional important advance in the art would be to provide a vacuum operated apparatus for donning and removing gloves in which the amount of vacuum pressure can be controlled so that the device can be used in different altitudes, and so that additional glove inflation is provided for users with larger hands.

It would be another significant advance in the art to provide an apparatus for donning and removing gloves in which the glove application area is large enough to comfortably fit larger hands with fingers outstretched, so that one single device can be used for people of all hand sizes. It would also be an advance to provide ambidextrous glove donning and removing apparatus such that one apparatus can be used for the right or left hand and for gloves that can fit either hand.

Still another important advance in the art would be to provide apparatus for donning and removing gloves which facilitates internal maintenance and cleaning of the apparatus.

Such apparatus and methods for donning and removing gloves are disclosed and claimed herein.

BRIEF SUMMARY AND OBJECTS OF THE INVENTION

The present invention is directed to apparatus and methods for easy donning and removal of elastomeric gloves. In one embodiment within the scope of the present invention, the apparatus includes a housing which defines a vacuum chamber and a vacuum pump chamber therein. A partition within the housing separates the vacuum chamber from the vacuum pump chamber. A passageway allows gaseous communication between the two chambers.

The vacuum chamber is large enough to accommodate an outstretched hand and has an opening through which the hand can pass. Through this opening, an elastomeric glove can be placed into the vacuum chamber such that the hand portion of the glove is suspended within the vacuum chamber and the wrist portion of the glove is remains outside the vacuum chamber. The glove is suspended from the opening by a stiffening ring about the wrist portion of the glove. The stiffening ring has a diameter larger than the diameter of the opening. With a glove suspended from the opening, vacuum pressure from within the vacuum chamber holds the glove and stiffening ring tight against the device, thereby sealing the opening. The vacuum chamber and opening are preferably angled such that insertion of a hand is comfortable and easy. The small, lightweight device can be placed upon a table or similar support.

The vacuum pump chamber houses a vacuum pump therein. Operation of the vacuum pump creates a vacuum within the interior of the vacuum chamber. Atmospheric pressure then causes the elastomeric glove suspended from the opening to become inflated. A vacuum pump speed control knob adjusts the speed of the vacuum pump, and therefore, allows the amount of vacuum pressure created and the amount of glove inflation obtained to be adjusted for given operating conditions.

A baffle is located within the vacuum chamber to direct the air flow to the vacuum pump. This baffle is supported by baffle legs which guide the glove fingers and assist in donning the gloves. The baffle may be removable for easy cleaning of the interior of the apparatus and of the baffle itself. As well as the baffle, the partition separating the vacuum chamber from the vacuum pump chamber also directs the air flow to the vacuum pump.

Also included with the apparatus is a foot-operated electrical switch for controlling the operation of the vacuum pump. A foot switch allows the user to don or remove the glove using only one hand, allowing the other hand to be free for other tasks, or if already gloved, to be free from any contact with unclean surfaces.

In another embodiment within the scope of the present invention, the upper surfaces of the housing are constructed of a clear material, such as plastic, that enables the interior of the vacuum chamber to be seen. A mirror may be positioned on the back wall of the vacuum chamber to further facilitate visual donning and removal of gloves.

It is therefore an object of the present invention to provide apparatus for donning gloves that is quick, easy, and convenient, and apparatus for removing gloves such that the gloves are not torn or inverted and so easily reused, and such that the user need not touch the exterior of the glove.

An additional object of the present invention is to provide apparatus for donning and removing gloves that is portable and that allows the vacuum pump speed to be controlled such that the apparatus can be used in various geographical locations and altitudes.

Another important object of the present invention is to provide apparatus for donning and removing gloves which would allow one-handed application and enhanced operating convenience. One possible means for this is a foot-operated electrical switch for controlling the operation of the pump.

A further object of the present invention is to provide apparatus for donning and removing gloves with the hand area large enough for the hand to move freely and comfortably, and angled such that insertion of the hand is easy and comfortable. One possible means for this is to have the vacuum chamber in a box shape rather than a cylindrical shape.

Still another object of the present invention is to provide apparatus for donning and removing gloves containing removable sections for easier maintenance and cleaning of the apparatus. In one embodiment within the scope of the present invention, the baffle is removable, allowing easy access to the interior of the vacuum chamber.

These and other objects and advantages will become more fully apparent from the following description and appended claims, taken in conjunction with the accompanying drawings, or may be learned from the practice of the invention.

BRIEF DESCRIPTION OF THE DRAWINGS

In order to more fully understand the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DETAILED DESCRIPTION OF THE PREFERRED EMBODIMENT

Figure 1:
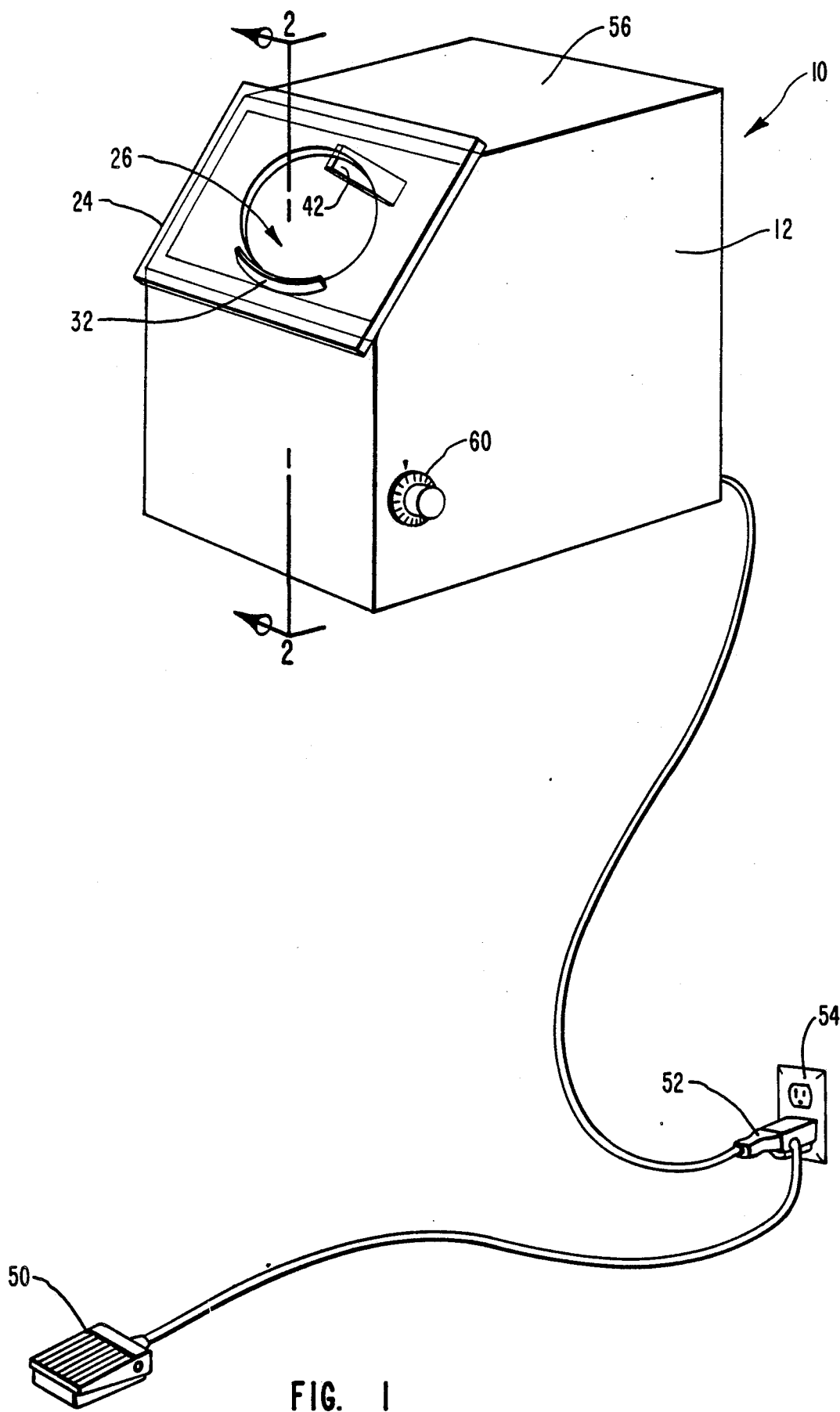
FIG. 1 is a perspective view of one possible glove application and removal apparatus within the scope of the present invention.
Figure 2:
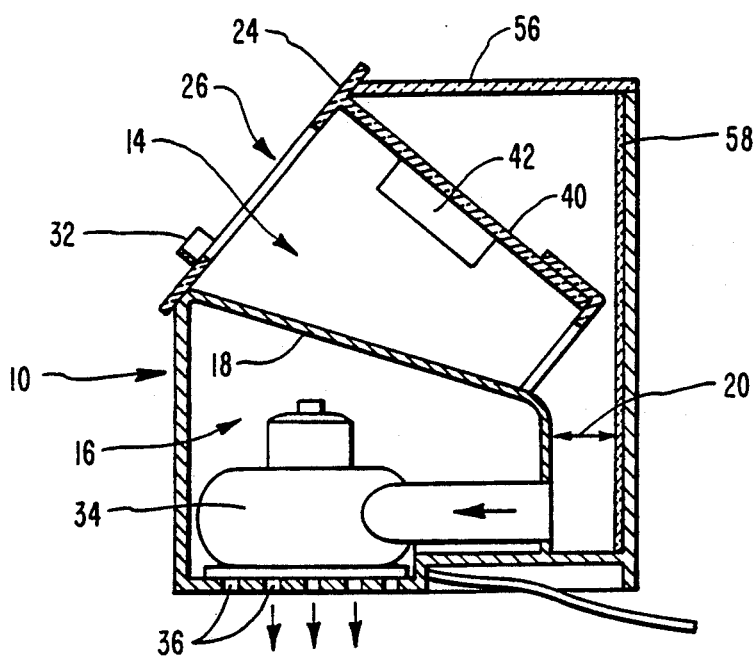
FIG. 2 is a cross-sectional view of the apparatus of FIG. 1 taken along line 2—2 of FIG. 1.

In FIGS. 1 and 2, one possible apparatus for donning and removing gloves within the scope of the present invention is illustrated and generally designated 10. Apparatus 10 includes housing 12 which defines vacuum chamber 14 and vacuum pump chamber 16 therein.

Vacuum chamber 14 is in gaseous communication with vacuum pump chamber 16. Vacuum chamber 14 is preferably of a size sufficient to accommodate an outstretched hand. In the embodiment within the scope of the present invention shown in FIG. 2, a partition 18 separates vacuum chamber 14 from vacuum pump chamber 16. A passageway 20 is located between partition 18 and housing 12 such that there is gaseous communication between the vacuum chamber and the vacuum pump chamber.

Lid 24 covers vacuum chamber 14. Lid 24 is preferably made of clear material, such as clear plastic, to permit full view of the interior of vacuum chamber 14. Lid 24 defines an opening 26 into the vacuum chamber through which a glove and user's hand are inserted. Opening 26 has a diameter sufficiently large to permit entrance of a hand into vacuum chamber 14. The lid and opening are preferably angled such that when the user is standing, his or her hand may be comfortable and easily inserted into the vacuum chamber.

Figure 3:
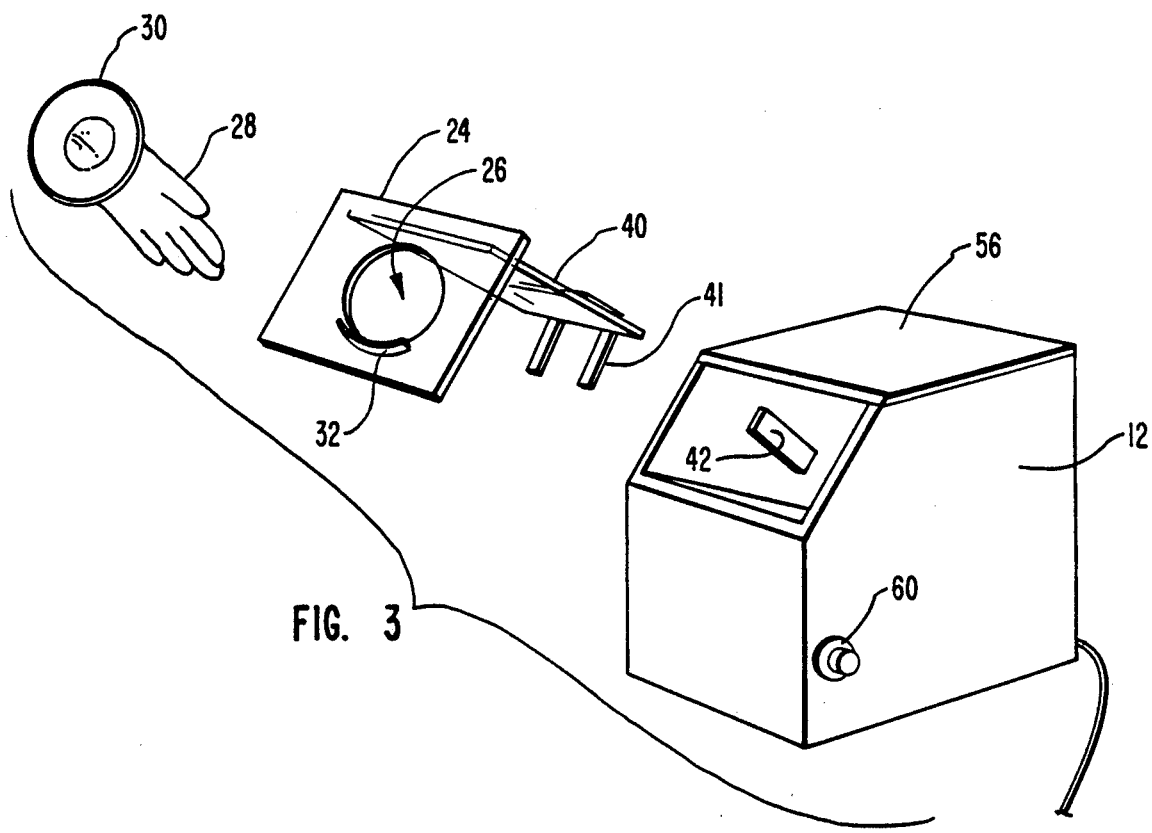
FIG. 3 is a perspective view of removable baffle and glove with stiffening ring.
Figure 4:
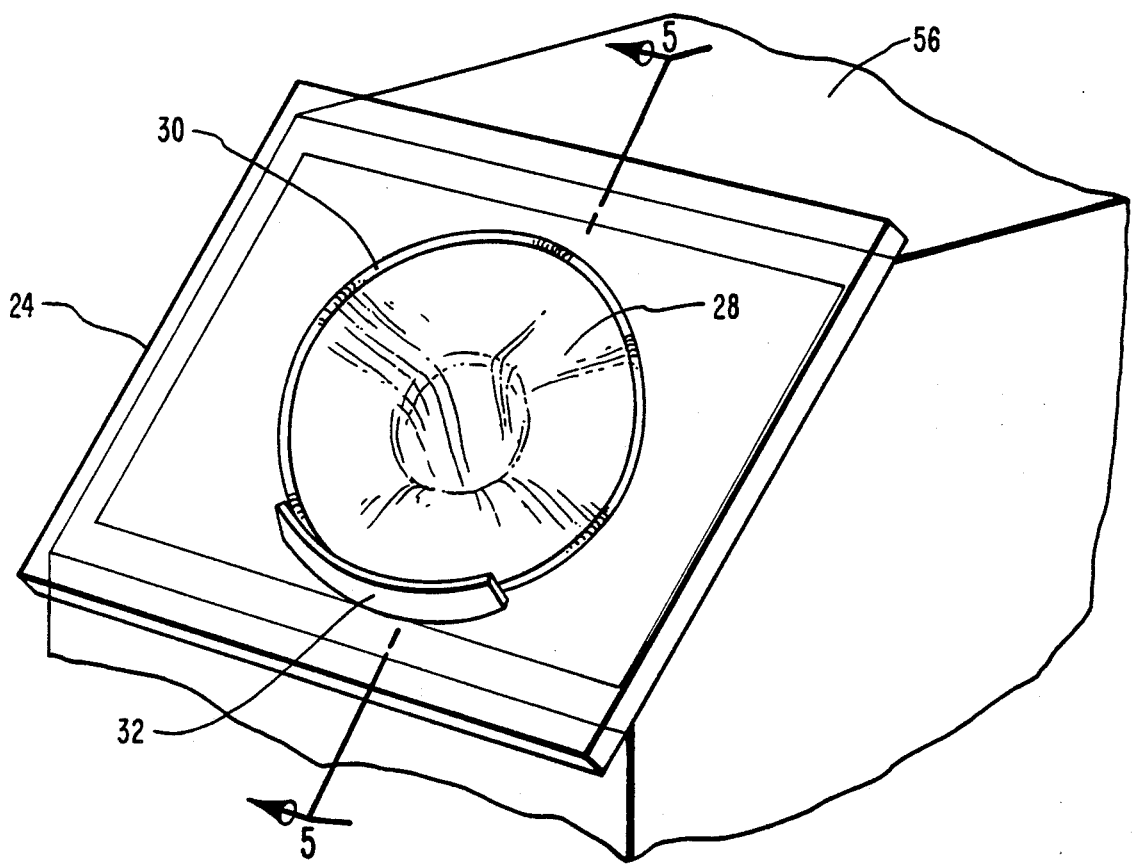
FIG. 4 is a partial perspective view of the apparatus shown in FIG. 1 having a glove with a stiffening ring positioned through the opening of the vacuum chamber.
Figure 5:
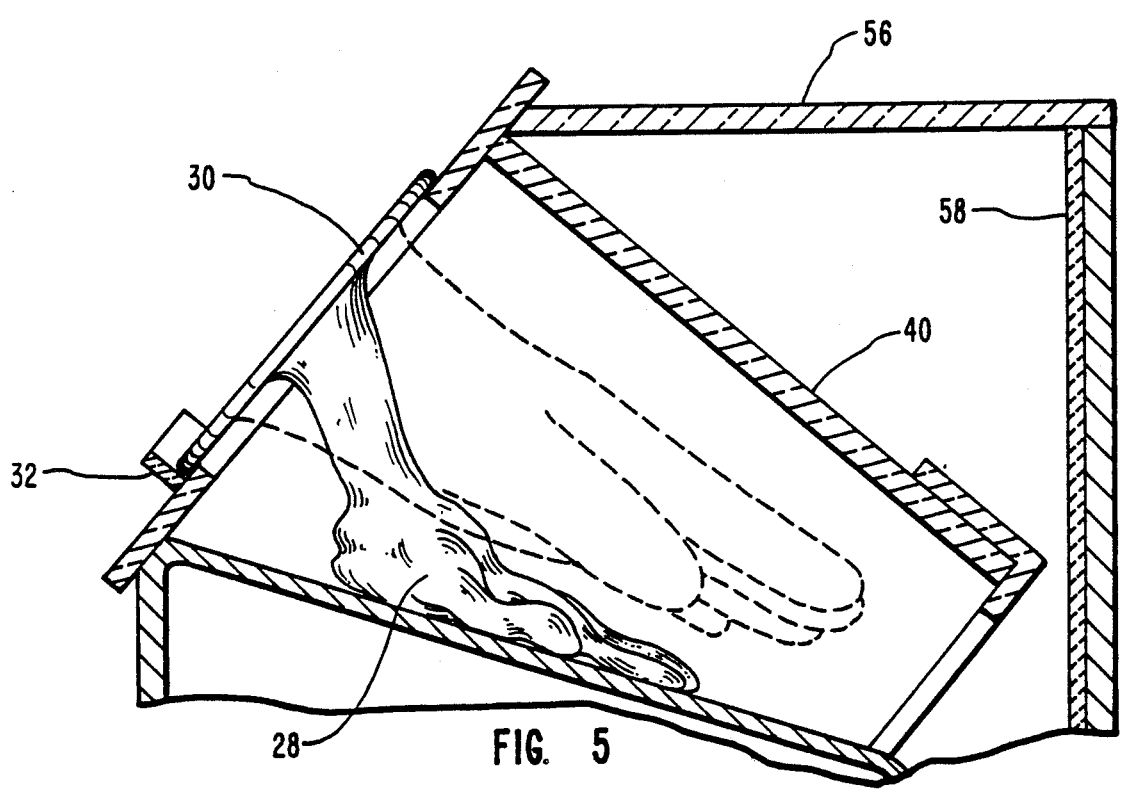
FIG. 5 is a cross-sectional view of the apparatus shown in FIG. 4 along line 5—5 of FIG. 4.

It is through opening 26 that an elastomeric glove 28 is placed within vacuum chamber 14. Elastomeric glove 28, as illustrated in FIG. 3, has a stiffening ring 30 around the wrist portion of the glove. The diameter of stiffening ring 30 is preferably greater than the diameter of opening 26 so that when the hand portion of elastomeric glove 28 is placed within the vacuum chamber, the wrist portion with stiffening ring 30 remains outside the vacuum chamber. This positioning is best illustrated in FIGS. 4 and 5.

One possible means within the scope of this invention for maintaining proper positioning of stiffening ring 30 outside the vacuum chamber is a small ledge 32 located below opening 26. Stiffening ring 30 rests on ledge 32 when glove 28 is placed into the vacuum chamber. This is best illustrated in FIG. 4. It will be appreciated that those skilled in the art may use other mechanisms for maintaining proper positioning of stiffening ring 30 around opening 26.

Once glove 28 is placed within vacuum chamber 14, a vacuum pump 34 can be operated to create a vacuum within vacuum chamber 14. FIG. 2 illustrates vacuum pump 34 positioned within vacuum pump chamber 16. When vacuum pump 34 is operating, partition 18 guides the flow of air from vacuum chamber 14 to vacuum pump 34 and out through ventilated floor panel 36.

A removable baffle 40 within vacuum chamber 14 also guides the flow of air. At least two baffle legs 41 separate baffle 40 from partition 18. Baffle legs 41 are spaced apart and positioned such that fingers of an outstretched hand within the vacuum chamber are separated by the baffle legs. It has been found that the baffle legs assist and facilitate in donning gloves. Baffle 40 is held in place within vacuum chamber 14 by two baffle supports 42. Baffle 40 narrows vacuum chamber 14 and directs the vacuum so that the glove is inflated more evenly.

In one preferred embodiment within the scope of the present invention shown in FIG. 3, removable baffle 40 is connected to lid 24 in such a way that the whole section is removable for easy cleaning of both the baffle and the interior of vacuum chamber 14. Removable baffle 40 slides easily along baffle supports 42.

It is also within the scope of the present invention to have an embodiment in which a non-removable baffle is used in combination with a hinged wall or top portions of housing 12. A hinged wall or top portion would make the interior of the device readily accessible.

Another important feature within the scope of the present invention is a foot operated electrical switch 50 for controlling the operation of the vacuum pump. Foot switch 50 allows the user to obtain vacuum pressure "on demand" during donning and removal of the gloves and frees the other hand for other use. Of course, it will be appreciated that well known hand operated electrical switches will also function adequately to control the operation of the vacuum pump. Nevertheless, it has been found that foot switch 50 significantly enhances the efficiency of the process for applying gloves. Although foot switch 50, as illustrated in FIG. 1, is positioned between electrical plug 52 and an electrical wall socket 54, it will be appreciated that one skilled in the art could design a foot switch coupled directly to the vacuum pump which performs the same function.

Another important feature within the scope of the present invention is the ability to view the glove donning process. This viewing is made possible by constructing lid 24 and top portion 56 of housing 12 of a clear material that permits full view of hand and glove after insertion into vacuum chamber 14. In addition, a mirror 58 positioned against the rear wall of vacuum chamber 14 further facilitates visual donning and removal of gloves.

An additional important feature within the scope of the present invention is a control knob 60, pictured in FIGS. 1 and 3, which permits manual control of the vacuum pump operation speed. Control knob 60 adjusts the amount of vacuum pressure created by vacuum pump 34 as needed for each use. The ability to adjust the vacuum pressure to higher and lower settings can be very advantageous for a glove donning apparatus because the amount of vacuum needed to properly inflate a glove varies depending on the altitude at which the device is being used. Therefore, a control knob capable of adjusting the vacuum pressure for each use would allow the device to function properly in all geographical locations of all altitudes. The use of the device would not be confined to the area for which the device was made. Further, the control knob would allow for additional glove inflation for users with extra large hands.

FIGS. 4 and 5 illustrate inflation of an elastomeric glove by one possible apparatus within the scope of the present invention. As shown in FIG. 4, elastomeric glove 28 is preferably positioned within vacuum chamber 14 such that the hand portion of the elastomeric glove passes through opening 26 and remains inside the vacuum chamber while the stiffening ring portion of the glove remains positioned around opening 26 on the outside of vacuum chamber 14. One possible way of maintaining the stiffening ring in proper position around opening 26 is with ledge 32. When properly positioned around opening 26, the stiffening ring and elastomeric glove act to seal vacuum chamber 14 when vacuum pump 34 is operated. In operation, atmospheric pressure causes the glove to inflate, as shown with phantom lines in FIG. 5. Once the glove is inflated, the user may easily insert his or her hand into the glove.

In summary, it will be appreciated that the present invention provides an apparatus for fast and convenient donning and removal of gloves. Apparatus within the scope of the invention require use of only one hand for donning a glove, and a single apparatus can be used for both right and left hands and by people having different hand sizes. Access to the apparatus is comfortable and easy due to the angle of the opening to the vacuum chamber. The apparatus for donning and removing gloves disclosed herein permit easy interior cleaning and maintenance, and the apparatus can be used in a variety of geographical locations and altitudes.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. An apparatus for donning gloves comprising:
   a housing defining a vacuum chamber and a vacuum pump chamber therein, said vacuum chamber having a size sufficient to accommodate an outstretched hand and having an opening sufficiently large to pass a hand therethrough, and said vacuum pump chamber in gaseous communication with said vacuum chamber, said housing having a clear top portion to enable viewing of the interior of the vacuum chamber;
   a vacuum pump within the vacuum pump chamber for creating a vacuum within the vacuum chamber;
   means for positioning an elastomeric glove through the vacuum chamber opening such that the hand portion of the glove is within the vacuum chamber and such that the wrist portion of the glove is outside the vacuum chamber, said elastomeric glove having a stiffening ring about the wrist portion of the glove, said stiffening ring having a diameter greater than the diameter of said opening;
   means for controlling the vacuum pump operation speed such that the vacuum pressure created within the vacuum chamber is capable of being adjusted to both higher and lower settings;
   a baffle located within the vacuum chamber for directing the airflow to the vacuum pump; and
   means for controlling the operation of the vacuum pump.

2. An apparatus for donning gloves as defined in claim 1, wherein the baffle is removable.

3. An apparatus for donning gloves as defined in claim 1, wherein the stiffening ring is removably attached to the glove.

4. An apparatus for donning gloves as described in claim 1, wherein the means for properly positioning the stiffening ring portion of the elastomeric glove over the opening of the vacuum chamber comprises a small ledge protruding from the exterior surface of the cover of the vacuum chamber around the bottom of the opening.

5. An apparatus for donning gloves as described in claim 1, wherein the vacuum pump is electrically operated.

6. An apparatus for donning gloves as described in claim 5, wherein the means for controlling the operation of the vacuum pump is a foot-operated electrical switch.

7. An apparatus for donning gloves as described in claim 1, further comprising a mirror positioned against the rear wall of the vacuum chamber to further facilitate viewing of the interior of the vacuum chamber.

8. An apparatus for donning gloves as described in claim 7, wherein the clear portion of the housing is constructed of plastic.

9. An apparatus for donning gloves as described in claim 1, wherein the vacuum chamber opening is angled to facilitate insertion of a user's hand into the vacuum chamber.

10. An apparatus for donning and removing gloves comprising:
    a housing defining a vacuum chamber and a vacuum pump chamber therein, said vacuum chamber having a size sufficient to accommodate an outstretched hand and having an opening sufficiently large to pass a hand therethrough, and said vacuum pump chamber in gaseous communication with said vacuum chamber, wherein a top portion of the housing is clear to enable viewing of the interior of the vacuum chamber;
    an electrically operated vacuum pump within said vacuum pump chamber for creating a vacuum within the vacuum chamber;
    means for positioning an elastomeric glove through the vacuum chamber opening such that the hand portion of the glove is within the vacuum chamber and such that the wrist portion of the glove is outside the vacuum chamber, said elastomeric glove having a stiffening ring about the wrist portion of the glove, said stiffening ring having a diameter greater than the diameter of said opening;
    an electrical control knob for manually adjusting the vacuum pump speed such that the vacuum pressure created within the vacuum chamber can be adjusted to both higher and lower settings;
    a baffle located within the vacuum chamber for directing airflow to the vacuum pump, said baffle being removable; and,
    an electrical switch for controlling the operation of the vacuum pump.

11. An apparatus for donning and removing gloves as described in claim 10, wherein the stiffening ring is removably attached to the glove.

12. An apparatus for donning and removing gloves as described in claim 10, wherein the means for properly positioning the stiffening ring portion of the elastomeric glove around the opening of the vacuum chamber comprises a small ledge protruding from the exterior surface around the bottom of the opening.

13. An apparatus for donning and removing gloves as described in claim 10, wherein the electrical switch for controlling the operation of the vacuum pump is foot operated.

14. An apparatus for donning and removing as described in claim 10, wherein the clear portion of the housing is constructed of plastic.

15. An apparatus for donning and removing gloves as described in claim 10, further comprising a mirror positioned against the rear wall of the vacuum chamber.

16. An apparatus for donning and removing gloves comprising:
    a housing defining a vacuum chamber and a vacuum pump chamber therein, said vacuum chamber having a size sufficient to accommodate an outstretched hand and having an opening sufficiently large to pass a hand therethrough, said vacuum pump chamber in gaseous communication with said vacuum chamber, and said housing having a top portion constructed of clear material;

an electrically operated vacuum pump within said vacuum pump chamber for creating a vacuum within the vacuum chamber:

means for positioning an elastomeric glove through the vacuum chamber opening such that the hand portion of the glove is inside the vacuum chamber and such that the wrist portion of the glove is outside the vacuum chamber, said elastomeric glove having a plastic stiffening ring about the wrist portion of the glove, said stiffening ring having a diameter greater than the diameter of said opening;

an electrical control knob for manually adjusting the vacuum pump speed such that the vacuum pressure created within the vacuum chamber can be adjusted to both higher and lower settings;

a baffle located within the vacuum chamber for directing airflow to the vacuum pump, said baffle being removable;

a foot-operated electrical switch for controlling the operation of the vacuum pump; and a mirror positioned against the rear wall of the vacuum chamber.

* * * * *